United States Patent [19]

Monchalin

[11] Patent Number: 4,607,341

[45] Date of Patent: Aug. 19, 1986

[54] DEVICE FOR DETERMINING PROPERTIES OF MATERIALS FROM A MEASUREMENT OF ULTRASONIC ABSORPTION

[75] Inventor: Jean-Pierre Monchalin, Montreal, Canada

[73] Assignee: Canadian Patents and Development Limited, Ottawa, Canada

[21] Appl. No.: 586,323

[22] Filed: Mar. 5, 1984

[51] Int. Cl.[4] .................. G01N 29/00; G06F 15/20
[52] U.S. Cl. ............................. 364/557; 364/508; 73/602; 73/599
[58] Field of Search .............. 364/557, 507, 508, 571; 73/599, 602, 646; 374/117, 170

[56] References Cited

U.S. PATENT DOCUMENTS

| | | | |
|---|---|---|---|
| 3,858,437 | 1/1975 | Jarzynski et al. | 73/599 |
| 3,861,200 | 1/1975 | Dory | 73/599 |
| 4,454,585 | 6/1984 | Ele | 364/507 |
| 4,543,827 | 10/1985 | Tominaga et al. | 364/508 |

OTHER PUBLICATIONS

Journal of Metals, Sep. 1979, Edmund G. Henneke, II, et al., Virginia Polytechnic Institute and State University, Blacksburg, Va. "Thermography—An NDI Method for Damage Detection", pp. 11-15.

K. L. Reifsnider et al., Engineering Science and Mechanics Department Virginia Polytechnic Institute and State University, Blacksburg, Virginia 240 61, "The Mechanics of Vibrothermography", pp. 249-276.

Primary Examiner—Gary Chin
Attorney, Agent, or Firm—Robic, Robic & Associates

[57] ABSTRACT

A method which determines at least one property of a material by measuring the ultrasonic absorption in this material. In carrying out this method, the material is subjected to an ultrasonic wave having an intensity varying in time. Such a method can be performed by measuring a temperature modulation, produced by absorption of the ultrasonic wave in a probed region of the material, at a surface area corresponding to this probed region, by measuring the ultrasonic power over the probed region, and by calculating the ultrasonic absorption in this probed region from the measured surface temperature modulation and the measured ultrasonic power for the purpose of determining at least one property of the material. Of course, the calculated ultrasonic absorption is representative of this material property. The method can also be carried out by subjecting the material to an external cause for varying its ultrasonic absorption, by measuring a relative variation, due to the external cause, of the temperature modulation at a surface area of the material corresponding to a region of this material subjected to the ultrasonic wave, and by measuring a variation of attenuation of the ultrasonic wave in the material due to the external cause. Thereafter, the ultrasonic absorption in the material is calculated from the measured relative variation of the temperature modulation and from the measured attenuation in order to determine at least one property of the material.

45 Claims, 7 Drawing Figures 4,607,341

DEVICE FOR DETERMINING PROPERTIES OF MATERIALS FROM A MEASUREMENT OF ULTRASONIC ABSORPTION

The present invention relates to the determination of at least one property of a material using a measurement of the ultrasonic absorption in this material.

A method for detecting defects in test pieces is known under the name of "VIBROTHERMOGRAPHY". This known method consists in the study of heat patterns produced by the energy dissipation which occurs when a specific vibratory excitation is applied to the test piece. More specifically, "VIBROTHERMOGRAPHY" is a variant of the thermography, which refers to the mapping of isotherms (countours of equal temperature) over a surface, in which the thermographic (heat) patterns to be studied are recorded and observed in real time during such a specific vibratory excitation. "VIBROTHERMOGRAPHY" is a useful non destructive test method for detecting defects in materials. However, it cannot be efficiently used to measure or at least give some information on the properties of these materials.

An object of the present invention is therefore to provide an ultrasonic technique which can be used to determine properties of a material other than defects.

According to the present invention, there is provided a method for determining at least one property of a material by measuring ultrasonic absorption in this material, the ultrasonic absorption being representative of said at least one property, such a method comprising the steps of:

subjecting a probed region of the material to an ultrasonic wave having an intensity varying in time;

measuring a temperature modulation at a surface area of the material, this surface area corresponding to the probed region, and the surface temperature modulation being produced by absorption in the probed region of the ultrasonic wave;

measuring an ultrasonic power over the probed region; and calculating the ultrasonic absorption in the probed region from the measured surface temperature modulation and the measured ultrasonic power for the purpose of determining said at least one property.

In accordance with the present invention, there is also provided a method for determining at least one property of a material by measuring ultrasonic absorption in the material, the ultrasonic absorption being representative of said at least one property, such a method comprising the steps of:

subjecting the material to an ultrasonic wave having an intensity varying in time:

subjecting the material to an external cause for varying the ultrasonic absorption of the material;

measuring a relative variation of a temperature modulation at a surface area of the material, this surface area corresponding to a region of the material subjected to the ultrasonic wave, the temperature modulation being generated by absorption of the ultrasonic wave in the material, and the relative variation of the temperature modulation being due to the external cause and being representative of a relative variation of ultrasonic absorption in the material;

measuring a variation of attenuation of the ultrasonic wave in the material due to the external cause; and calculating the ultrasonic absorption in the material from the measured relative variation of the temperature modulation and from the measured attenuation variation for the purpose of determining said at least one property.

According to the present invention, there is further provided a device for determining at least one property of a material by measuring ultrasonic absorption in the material, this ultrasonic absorption being representative of said at least one property, such a device comprising:

means for generating an ultrasonic wave having an intensity varying in time, and for subjecting a probed region of the material to this ultrasonic wave;

means for measuring a temperature modulation at a surface area of the material, this surface area corresponding to the probed region, and the surface temperature modulation being produced by absorption in the probed region of the ultrasonic wave;

means for measuring an ultrasonic power over the probed region; and means for calculating the ultrasonic absorption in the probed region from the measured surface temperature modulation and the measured ultrasonic power for the purpose of determining said at least one property.

In accordance with the present invention, there is also further provided a device for determining at least one property of a material by measuring ultrasonic absorption in this material, the ultrasonic absorption being representative of said at least one property, such a device comprising:

means for generating an ultrasonic wave having an intensity varying in time, and for subjecting the material to the ultrasonic wave;

means for subjecting the material to an external cause, this external cause changing the ultrasonic absorption of the material;

means for measuring a relative variation of a temperature modulation at a surface area of the material, this surface area corresponding to a region of the material subjected to the ultrasonic wave, the temperature modulation being generated by absorption of the ultrasonic wave in the material, and the relative variation of the temperature modulation being due to said external cause and being representative of a relative variation of ultrasonic absorption in the material;

means for measuring a variation of attenuation of the ultrasonic wave in the material due to the external cause; and means for calculating the ultrasonic absorption in the material from the measured relative variation of the temperature modulation and from the measured attenuation variation for the purpose of determining said at least one property.

The objects, advantages and other features of the present invention will become more apparent from the following non-restrictive description of preferred embodiments thereof, made in conjunction with the accompanying drawings in which.

Figure 1:
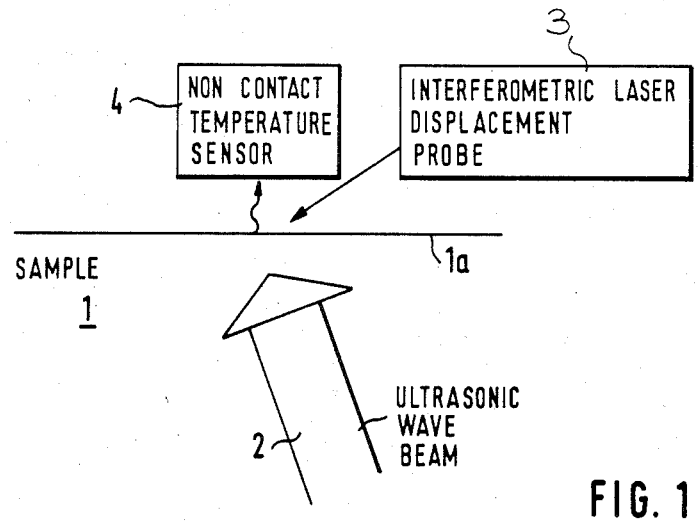
FIG. 1 illustrates the basic principle of the sensing operation carried out by the method and apparatus according to the present invention.

Referring now to FIG. 1 of the drawings, the specimen or sample 1 to be studied is subjected to an ultrasonic wave beam shown schematically at 2 and generated by an appropriate ultrasonic source, and a suitable temperature sensor 4 of the non-contact type monitors the temperature variation at the surface $1_a$ of the sample 1, this sample 1 being heated through an oscillation of the particles of its material caused by the ultrasonic wave.

This temperature variation is related to an absorption of ultrasounds in the sample 1 below the surface $1_a$ at a depth which depends on the time variation of the ultrasonic wave beam 2 from the ultrasonic source and the time interval between two consecutive temperature measurements through the sensor 4. For example, if the ultrasonic source generates a pulsed ultrasonic wave beam 2 (time duration of a few microseconds), the temperature measured through the sensor 4 immediately after the ultrasonic beam pulse will relate to an ultrasonic absorption at the surface $1_a$, whereas the temperature measured through the sensor 4 after a time $\Delta t$ will relate to an ultrasonic absorption at a depth equal to $v\Delta t$, v being the speed of propagation of thermal waves produced by the ultrasonic absorption in the sample 1. If the ultrasonic source generates an ultrasonic wave beam 2 continuously modulated in intensity (or pulsed) at a frequency f, the surface temperature measured through the sensor 4 at the same frequency relates to an ultrasonic absorption within a layer below the surface $1_a$ having a thickness of about one wavelength of the thermal waves produced by the ultrasonic absorption in the sample 1. The apparatus of FIGS. 4 and 5 uses this latter surface temperature measurement method as will be seen hereinabove. The thickness of the layer corresponds typically to a depth of a few millimeters below the surface $1_a$ at a modulation frequency of a few hertz in most metals and to an order of magnitude smaller depth below the surface $1_a$ in less heat conductive materials such as plastics and ceramics. Exact mathematical relations between the temperature variation of the surface $1_a$ and the heat source (in this case produced by absorption of ultrasounds) can be found or derived from text books on heat transfer such as "Conduction of heat in solids", by H. S. Carslaw and J. C. Jeager, Oxford Press (1959), or textbooks on photoacoustics or photothermal techniques such as "Photoacoustics and Photoacoustic Spectroscopy", by A. Rosencwaig, J. Wiley (1980).

The temperature sensor 4 used in the present invention should be of the non-contact type, since extraneous heat can be produced by any bonding agent provided between the temperature sensor 4 and the specimen or sample 1.

A very convenient type of temperature sensor is formed with an infrared detector which views the specimen or sample surface $1_a$, and with a device allowing a calibration of the temperature sensor according to the surface emissivity. A temperature sensor comprising an infrared detector and a calibrating device used in the apparatus of FIGS. 4 and 5 as well as the way to conduct a temperature measurement independently of the surface emissivity will be described in more details hereinafter with reference to these FIGS. 4 and 5.

Figure 2:
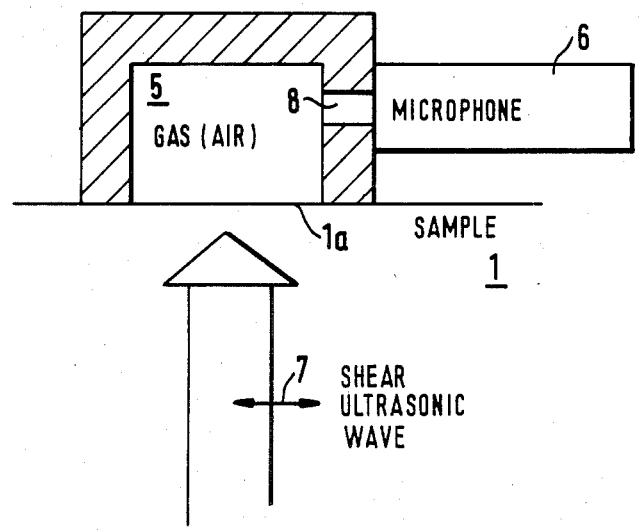
FIG. 2 shows an embodiment for a non-contact type temperature sensor shown in FIG. 1 comprising a closed cell and a microphone, which embodiment can be used to detect the absorption of an ultrasonic shear wave at normal incidence.

However, another very sensitive embodiment for the non-contact temperature sensor 4 of FIG. 1 which can also be used in the present invention is shown on FIG. 2. This embodiment comprises a closed cell 5 filled with gas (for example ambiant air) and is provided with a microphone 6. It is known that, for such a sensor, the pressure variation within the cell 5 detected through an aperture 8 by the microphone 6 is directly proportional to the temperature variation at the surface $1_a$ of the sample 1 (see for example "Photoacoustics and Photoacoustic Spectroscopy" by A. Rosencwaig, J. Wiley (1980)). The temperature sensor of FIG. 2 is mostly useful for shear waves at normal incidence shown for example at 7, since in other cases (incline shear wave or compressional wave) a part of the ultrasonic energy is coupled into the gas within the cell 5 and produces extraneous heat.

Figure 3:
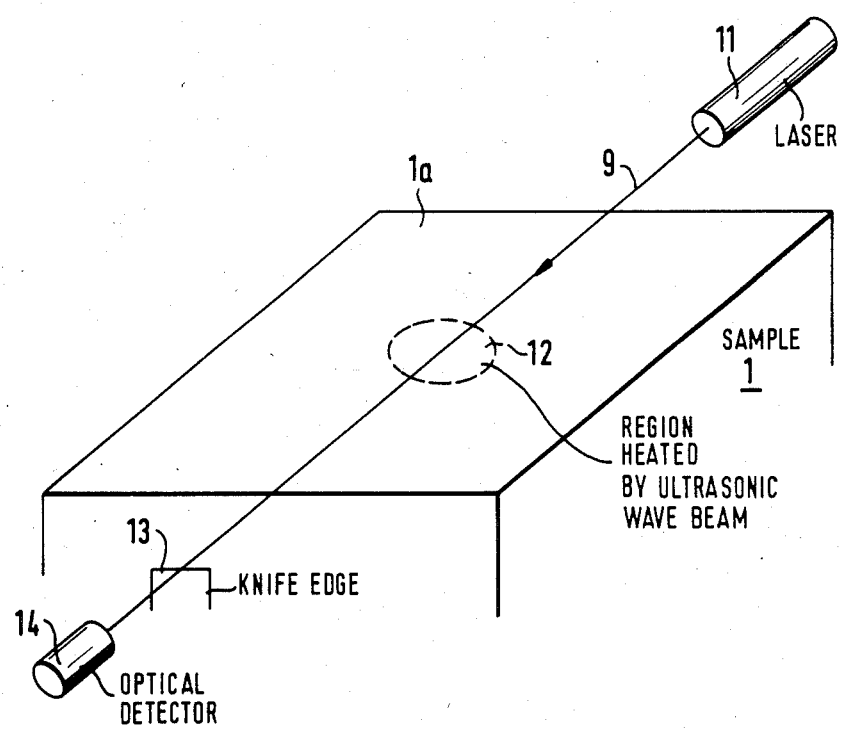
FIG. 3 shows another embodiment for the noncontact type temperature sensor of FIG. 1 using the deflection of a laser beam to determine the temperature of a surface (mirage effect)

A further embodiment for the non-contact temperature sensor 4 of FIG. 1, which can be utilized in the present invention, uses as shown on FIG. 3 the deflection of a laser beam 9 generated by a laser 11 and propagating closed to the surface $1_a$ of a specimen or sample 1, and has been described in the following papers: "Thermo-optical spectroscopy: Detection by the mirage effect", by A. C. Boccara, D. Fournier and J. Badoz in Applied Physics Letters, pp. 130–132, vol. 36 (1980), and "Photothermal spectroscopy using optical beam probing: Mirage effect", by J. D. Murphy and L. C. Aamodt in the Journal of Applied Physics, pp. 4580–4588, vol. 51 (1980). The heat at the surface $1_a$ produced in a probed region 12 heated by an ultrasonic wave beam deflects the laser beam 9, which deflection is function of the temperature at the surface $1_a$ corresponding to the heated region 12. In a known manner, a knife edge 13 along with an optical detector 14 allows to determine this deflection and thereby to measure the temperature at the surface $1_a$ of the sample 1 corresponding to the probed region 12.

Figure 4:
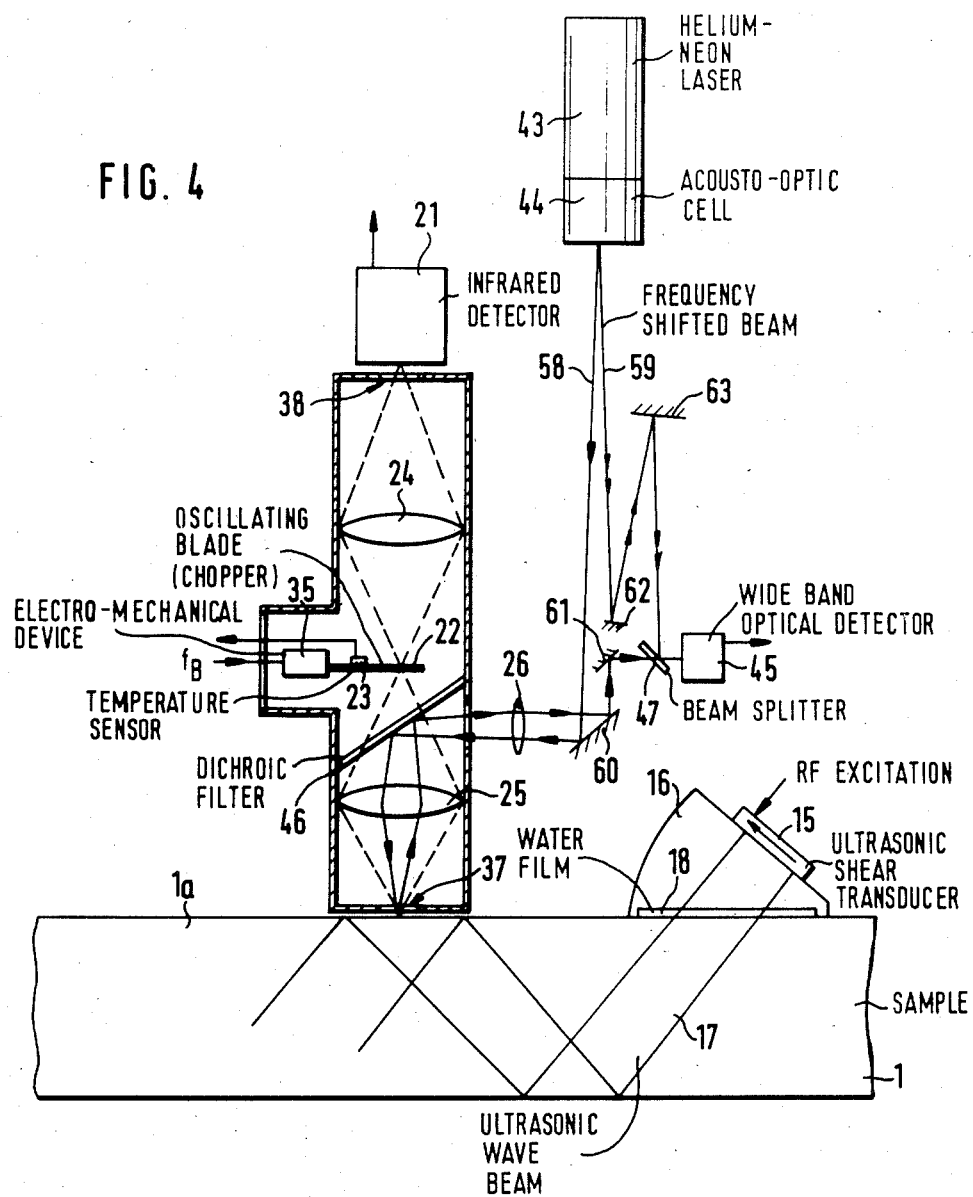
FIGS. 4 and 5 show a versatile embodiment for an ultrasonic absorption meter apparatus carrying out into practice the present invention.
Figure 5:
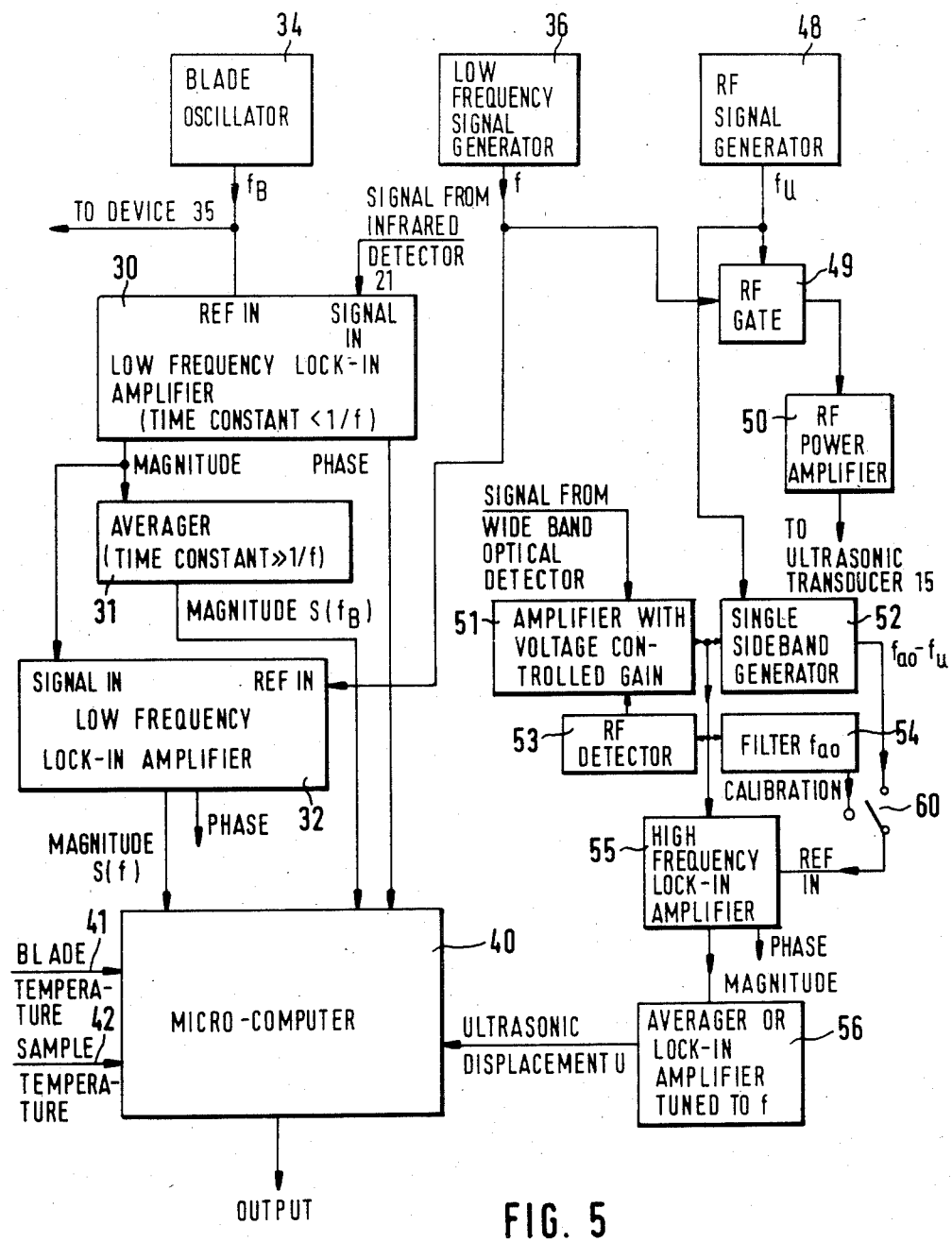

Since it is rather difficult to determine the ultrasonic power in the probed region or volume subjected to the ultrasonic wave beam 2 from the amplitude of the voltage applied for example to an ultrasonic transducer forming the ultrasonic source, the level of this ultrasonic power being determined and used by the apparatus of FIGS. 4 and 5, the present invention may use as illustrated on FIG. 1 an interferometric laser displacement probe 3 to determine a displacement of the surface $1_a$ of the sample 1 at the center of the area of the surface $1_a$ corresponding to the probed region subjected to the ultrasonic wave beam 2. Since this latter measurement is contactless, no extraneous heat is produced. From the knowledge of the shape of the ultrasonic wave beam 2 and the incidence angle of this beam, it is possible to relate by calculation this measured displacement to the ultrasonic power in the probed region or volume subjected to the ultrasonic wave beam.

The interferometric probe 3 can be basically for example a Michelson interferometer and uses a small helium-neon laser. It may be of the homodyne type (the two arms of the interferometric probe have a same optical frequency) or of the heterodyne type (the frequency in one of the two arms of the interferometric probe is shifted). An heterodyne design is preferred since it is known that in such a case, the probe 3 can be made easily immuned from ambiant vibrations, without active stabilization of the path length difference between the two arms of the interferometric probe as will become apparent from the following description. A method for making immuned from ambiant vibrations an heterodyne type interferometric probe is outlined for example in the article by R. M. De La Rue, R. F. Humphryes, I. M. Mason and E. A. Ash in the Proceedings of the Institute of Electrical Engineers (England), vol. 119, 1972, pp. 117–126, which method will be exposed in more details hereinafter. The interferometric probe of the absorption meter apparatus will also be further elaborated with reference to FIGS. 4 and 5.

Other methods which require contact to the sample of some kind can also eventually be considered to measure the ultrasonic power in the probed region. One method may use for example a phase insensitive ultrasonic receiver based on the acousto-electric effect in a cadmium sulfide crystal as described in the article entitled "Phase insensitive acoustoelectric transducer", by J. S. Heyman in the Journal of the Acoustical Society of America, Vol. 64, page 243, 1978. Another possible method is to cover the probed surface of the sample 1 by a highly ultrasonic absorbing tape or paint layer and to measure the temperature variation with the non-contact temperature sensor. In the case of metal samples, a black plastic sticky tape would be appropriate and convenient for this purpose.

A versatile ultrasonic absorption meter apparatus carrying out into practice the present invention is illustrated in detail on FIGS. 4 and 5. This apparatus can be scanned over for example a plate constituting the sample 1 to find regions where the mechanical properties of the plate such as cold work, residual stress or state of fatigue are changed thereby causing a change in the ultrasonic absorption of the material of this plate. This meter apparatus can also be used to compare the ultrasonic absorption of different specimens or samples in order to detect differences in mechanical properties of these samples. Absolute measurements of ultrasonic absorption can be performed knowing the ultrasonic beam profile and making analytical or numerical calculations in order to relate the surface temperature modulation and the surface displacement which can be sensed as above to the ultrasonic absorption and power. In many cases, it is also possible to calibrate the absorption meter apparatus. For example, one may use a variant of the technique mentioned below which determines the ultrasonic absorption by varying an external parameter (magnetic field, stress . . . ) and by using the result of a conventional attenuation measurement.

The meter apparatus sketched in FIGS. 4 and 5 which uses state of the art ultrasonic, optical and electronic technology plus several innovative features will now be described in details.

The meter apparatus includes an efficient and troubleless generator of ultrasonic wave beam from a moderate to a high power inside the specimen or sample 1. As shown in FIG. 4, a lithium-niobate ultrasonic shear transducer 15 is bonded on a metallic wedge 16 to generate a shear ultrasonic wave shown by the beam 17 inside the sample 1, which ultrasonic beam 17 is modulated in intensity at a frequency f. Such a lithium niobate transducer 15 is preferably used because of the low voltage required for its operation, and because of its efficient piezoelectric convertion as an emitter, its low absorption (the transducer does not heat), and for its easy operation on higher harmonics. For these reasons, quartz or ceramic transducers should not be used. A wedge 16 made of plastic material which is generally used in conventional ultrasonic techniques for non-destructive testing should also be excluded because of the large absorption of plastics. The coupling agent between the wedge 16 and the specimen or sample 1 is advantageously a water film 18, since water has the lowest ultrasonic absorption among coupling fluids. It is also possible to use a wedge 16 with a flat bottom which is pressed against the sample 1 with a few drops of water therebetween which make a very thin coupling interface or to use a wedge 16 with a continuously circulating water film between the wedge 16 and the sample 1. In such a case, the gap thickness (thickness of the water film) should be appropriate for an efficient transmission of the ultrasonic wave beam through this gap, i.e. the gap thickness should be approximately equal to half of an ultrasonic wavelength in water divided by the cosine of the incidence angle of the ultrasonic beam in the water gap.

In order to produce heat by ultrasonic absorption in the sample 1, a relatively high intensity surface wave can also be used and generated through a metallic wedge and a lithium-niobate shear transducer. For a steel sample 1, an efficient generation of such a surface wave is obtained with a 45° wedge made of brass. A compressional wave can also be generated using a lithium-niobate compression transducer mounted on a wedge made of aluminium, although in this case a shear ultrasonic wave is also generated at the same time inside the steel sample 1.

Figure 6A:
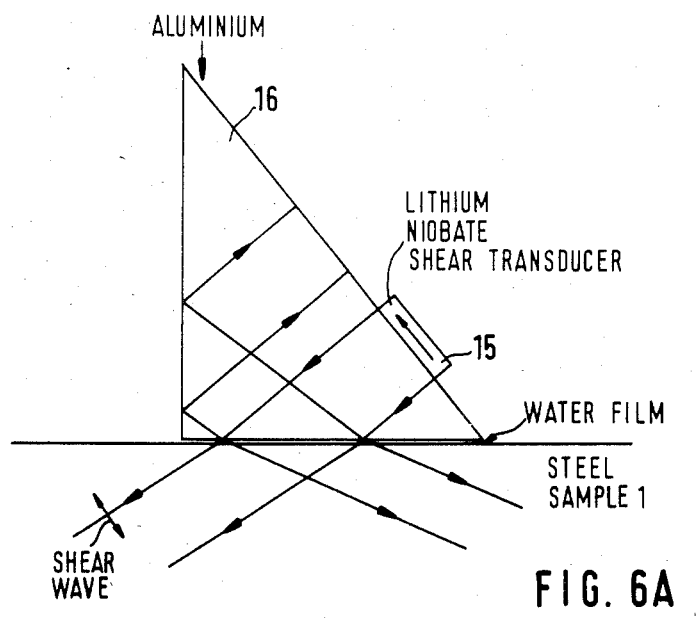
FIGS. 6A and 6B illustrate embodiments for an ultrasonic wave beam generator forming part of the apparatus of FIGS. 4 and 5, which embodiments use resonant wedges and can generate shear or surface ultrasonic waves.
Figure 6B:
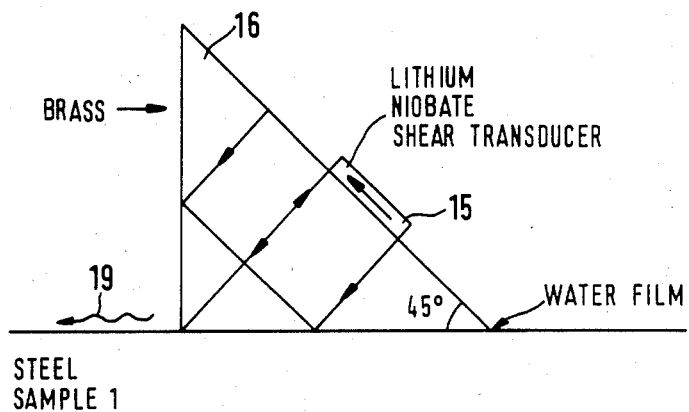

A very efficient wave generation is obtained by using an acoustically resonant wedge 16 as shown in FIG. 6A for the generation of a shear wave in the steel sample 1 and in FIG. 6B for the generation of a surface wave 19 on this steel sample 1. In these two cases, the wedge 16 has two perpendicular faces and the resonance is caused by reflexion from a same surface upon which the transducer 15 is bonded.

The meter apparatus of FIGS. 4 and 5 includes a radiometric system for measuring the modulation of the temperature at the surface $1_a$ of the sample 1. This radiometric system comprises an infrared detector 21 (pyroelectric, Golay or mercury cadmium telluride photoconductor for room temperature detection), an oscillating blade 22 acting as a radiation chopper, whose temperature is continuously measured through a temperature sensor 23, for example a thin film resistor deposited on the blade 22, and some optics, i.e. lenses 24 and 25 shown on FIG. 4 (or instead a light pipe) provided with apertures such as 37 and 38 for directing an infrared radiation from the surface $1_a$ to the detector 21 as illustrated by dotted lines, a dichroic filter 46 allowing passage of this infrared radiation. The light pipe unrepresented in FIG. 4 can be cylindrical or conical with its apex towards the detector 21 or the sample 1 according to the size of the detector 21 and the resolution on the sample 1. The temperature modulation at the surface $1_a$ caused by the ultrasonic wave beam 17 can be determined from the modulation of the amplitude of the signal at the output of the detector 21 produced by the chopping blade 22, which masks or not the infrared radiation from the sample 1, since the frequency $f_B$ of oscillation of the blade 22 is higher than the frequency f of modulation of the ultrasonic wave beam 17. The blade 22 is operated through an appropriate electromechanical device 35 (FIG. 4) activated through a blade oscillator 34 (FIG. 5) generating a signal of frequency $f_B$ supplied to this device 35.

Using two low frequency lock-in amplifiers 30 and 32 (FIG. 5), one amplifier 30 tuned to $f_B$ with a time constant 21 1/f and the other amplifier 32 tuned to f through their respective reference inputs REF IN supplied respectively by the blade oscillator 34 and a low frequency signal generator 36, it is possible to measure, as will be explained below, the temperature modulation at the surface $1_a$ independently of the local emissivity of the sample 1. As shown on FIG. 5, the amplifier 30 receives the signal from the output of the detector 21 while the amplifier 32 receives the magnitude output signal from the lock-in amplifier 30.

The radiation flux received by the detector 21 varies periodically at the frequency $f_B$ for example 1 kHz, between the flux $\epsilon Eg(T)$ slightly modulated at the frequency f located for example between 0.2 Hz and a few hundreds Hz when the blade 22 does not mask the aperture 37 and the flux $\epsilon_B E_B g(T_B)$ when the blade 22 masks the aperture 37. In these expressions, $\epsilon$ is the surface emissivity of the sample 1, T is the measured temperature of the sample 1 at its surface $1_a$, E is the étendue (or throughput i.e. the light gathering efficiency) of the viewing geometry when the blade does not mask the sample 1, $\epsilon_B$ is the emissivity of the blade 22, $E_B$ is the étendue of the viewing geometry when the blade 22 masks the aperture 37, $T_B$ is the temperature of the blade 22, $g(T)$ or $g(T_B)$ is a function which represents the response of the detector 21 and its front optics 24 and 25 to temperature. These responses are function of the spectral response of the detector 21 and of the spectral transmission of the front optics 24 and 25. Knowing these responses, the above function g will be obtained by convolution with the black body function (Planck's function). The function g can also be experimentally determined.

As it will become apparent from the following description, only the variation of the function g with the temperature T has an influence and not the exact value of this function g. In the case of a wide infrared band detector 21 (such as a pyroelectric or a Golay) and wide band optics 24 and 25, the function g is equal to $T^4$. The lock-in amplifiers 30 and 32 only detect harmonic terms. The amplifier 30 tuned to $f_B$ detects the signal $S_D(f_B)$ $[\epsilon Eg(T) - \epsilon_B E_B g(T_B)]a_1 \cos 2\pi f_B t$, where t represents time, $S_D$ is the sensitivity of the detector 21, $g(T) = g(\overline{T}) + g'(\overline{T})\delta T(t)$, $\overline{T}$ is the average sample temperature, g' is the derivative of g, $\delta T(t)$ is the variation of the surface temperature, and $a_1$ is a factor originating from the Fourier expansion of the function describing the variation of the infrared flux from the surface $1_a$ ($a_1$ depends on the chopping geometry). The lock-in amplifier 32 tuned to f detects $S_D(f_B) G g'(\overline{T})\epsilon E a_1 \tau \sqrt{2}\cos[2\pi ft+\phi]$, where $\tau$ is the rms value of the surface temperature modulation, and $\phi$ is the phase of this modulation with respect to that of the chopping blade 22 and G is the gain of the first lock-in amplifier 30. Let $S(f_B)$ be the average value of the output magnitude signal given by the first lock-in amplifier 30 and S(f) be the rms magnitude measured by the second lock-in amplifier (i.e. the rms magnitude at its input), then:

$$S(f_B) = S_D(f_B) G |\epsilon Eg(\overline{T}) - \epsilon_B E_B g(T_B)| a_1 \quad (1)$$

$$S(f) = S_D(f_B) G g'(\overline{T}) \epsilon E a_1 \tau \quad (2)$$

A third signal $S_o(f_B)$ is obtained when the radiometric system views a sample at a temperature T such that $g(T)$ is negligible (the sample can be cooled at nitrogen temperature or mounted on a thermoelectric cooler, $g(T) \cong 0$ being obtained by extrapolation):

$$S_o(f_B) = S_D(f_B) G \epsilon_B E_B g(T_B^o) a_1 \quad (3)$$

$T_B^o$ being the temperature of the blade 22 when the above experiment is performed. This measurement is carried out once for all for a given instrument. From the three previous equations (1), (2) and (3), it follows:

$$\tau = \frac{g(\overline{T})}{g'(\overline{T})} \frac{S(f)}{\frac{g(T_B)}{g(T_B^o)} S_o(f_B) \pm S(f_B)} \quad (4)$$

where the (+) sign applies when $\epsilon Eg(\overline{T}) > \epsilon_B E_B g(T_B)$ and the (−) sign in the reverse case (this can be found out from the phase of the infrared signal detected at the frequency $f_B$ with respect to the phase of the signal from the oscillator 34 producing the motion of the blade 22). As the change of temperature produced by the ultrasonic wave beam is small, $\overline{T} \cong T$, the temperature of the sample without ultrasonic excitation. If needed, the function g can also be found experimentally by plotting $S_o(f_B) \pm S(f_B)$ which is proportional to $g(T)$ as a function of the temperature of the sample 1. In doing that, one can assume that $T_B = T_B^o$, which can be realized, otherwise some iteration can be performed. $g(\overline{T})/g'(\overline{T}) \cong g(T)/g'(T)$ is a slowly varying function of the temperature T (for a broad infrared band detector 21, $g(\overline{T})/g'(\overline{T}) = \overline{T}4 \cong T/4$), so a single thermocouple or other temperature sensor mounted on the sample will be sufficient for measuring the value $\overline{T}$ entering in $g(\overline{T})/g'(\overline{T})$. In many cases, it will be simply the ambiant temperature. Therefore, knowing the temperature and frequency responses of the detector 21 (or having measured them), knowing the temperature of the blade 22 and the sample 1 and having performed previously an ultrasonic measurement on a sample at a low temperature, (for determining Eq. 3), the surface temperature modulation $\tau$ produced by the ultrasonic wave beam can be calculated from equation (4) independently of the surface emissivity and other factors. A micro-computer 40 is used to perform this calculation in response as shown on FIG. 5 to the phase signal from the amplifier 30, the magnitude signal S(f) from the amplifier 32, the magnitude signal $S(f_B)$ at the output of an averager 31 having a time constant $<< 1/f$, which signal $S(f_B)$ resulting from averaging of the magnitude signal from the amplifier 30 through the averager 31, a blade temperature signal 41 provided through the temperature sensor 23 (see FIG. 4), and a sample temperature /OVs/T/ signal 42 provided through for example the above-mentioned thermocouple or other temperature sensor. The phase information or signal provided by the lock-in amplifier 32 tuned to f can possibly be used to study a non-homogeneous sample in which the ultrasonic absorption varies with depth.

A third element of the absorption meter apparatus, is an interferometric displacement probe which measures the displacement of the surface $1_a$ of the sample 1 (see FIG. 4) at the ultrasonic frequency $f_u$ located for example between 0.2 to 25 MHz, which displacement being produced by the ultrasound. The interferometric displacement probe comprises as illustrated on FIG. 4 a helium-neon laser 43 along with an acousto-optic cell 44 for generating two laser beams 58 and 59 of different frequencies forming the two arms of the probe. This probe is of the above-mentioned heterodyne type as the frequency of the arm 59 generated through the helium-neon laser 43 is shifted by a frequency $f_{ao}$ equal for example to 40 MHz using the acousto-optic cell 44, the direction of this arm 59 being also modified through the cell 44. The first arm 58 which is unchanged in direction and frequency by the cell 44 is reflected a first time at 60, passes a first time through the lens 26, is reflected a first time on a dichroic filter 46, passes a first time through the lens 25, is reflected on the surface $1_a$ of the sample 1, passes a second time through the lens 25, is reflected again on the filter 46, passes a second time through the lens 26, is reflected again at 60, and finally is supplied to a wide-band optical detector 45 through a beam splitter 47 after reflection at 61. The second frequency shifted arm 59 is also supplied to the detector 45 after reflections at 62 and 63 and after reflection on the beam splitter 47. The different reflections carried out on the two arms of the probe are used for appropriately directing the arms 58 and 59 and for adjusting the length of the paths of these two arms.

The signal received by the detector 45 therefore appears as two side-bands $f_{ao} \pm f_u$, one of which ($f_{ao} - f_u$) is detected by a high frequency lock-in amplifier 55 tuned to $f_{ao} - f_u$ as described in more details hereinafter. This probe uses the principle outlined by R. M. De la Rue et al noted above, i.e. the carrier signal (40 MHz) used for the displacement measurement is derived from the optical signal, which enables the probe to be immune to the variations of optical paths caused by vibrations. However, instead of using a filter to select the side band as in De La Rue et al, which limits the generality of the scheme, the meter apparatus comprises a single side band generator 52 to generate a single side band from the optical carrier received through the wide band optical detector 45 and an amplifier with voltage controlled gain 51 and from a signal at the frequency $f_u$ generated by a RF generator 48 using state-of-art RF methods (for example a power divider combined with two mixers and 90° phase shifters). This single side band $f_{ao} - f_u$ is supplied to the lock-in amplifier 55 through a switch 60 and is used as reference signal to this high frequency lock-in amplifier 55. In order to compensate for fluctuations of the reflectivity into the reference beam 58 of the interferometer caused by vibrations, in order to operate automatically on samples of very different reflectivities and for a proper operation of the single side band generation scheme, the signal from the detector 45 is amplified to a constant level through the amplifier 51 with voltage-controlled gain. The voltage for controlling the gain is given through a RF detector 53 receiving the output signal of the amplifier 51. The calibration of the probe is performed by tuning the lock-in amplifier 55 to the carrier frequency $f_{ao}$ provided through a filter 54 filtering the signal from the amplifier 51 and a switch 60, and by measuring the signal at the carrier frequency $f_{ao}$ through the lock-in amplifier 55: as a simple derivation shows, the ratio of the side band signal to that of the carrier is equal to $2\pi U/\lambda$, where U is the ultrasonic displacement amplitude and $\lambda$ is the wavelength of the laser beam 58 used in the probe. This calibration is done once for all, since the automatic gain control of the amplifier 51 through the detector 53 will maintain the carrier signal arriving at the lock-in amplifier 55 at the same level. This probe, once calibrated, enable to scan over a surface and to obtain a direct reading of the displacement. Since ultrasound is modulated at the frequency f which can vary for example from 0.2 Hz to a few hundred Hz, the output of the lock-in amplifier 55 varies at the same frequency. In order to get a non-varying indication, the modulation of ultrasonic wave can be either turned off, or the output of the amplifier 55 is averaged through an averager 56 in order to get the mean value of the displacement U. In order to carry out this step, the averager 56 can be a lock-in amplifier tuned to the modulation frequency f. The probe oriented normally to the surface as shown in FIG. 4 measures the vertical displacement of the surface, which can be produced by a compressional wave, an inclined shear wave (as shown in FIG. 4), or a surface wave. In order to measure the displacement of a normally incident shear wave, the prove is inclined at an angle.

The amplitude U of the displacement measured by the interferometric probe and provided at the output of the averager 56 is sent to the micro-computer 40 which squares it. By dividing the surface temperature modulation $\tau$ by $U^2$ (U being the average amplitude of the measured displacement) through the computer 40, a signal proportional to absorption is obtained. In order to obtain the exact value of absorption, it is necessary to perform theoretical calculations through the computer which takes into account the ultrasonic wave beam profile, the distribution of the ultrasonic energy inside the probed region of the material and the thermal properties of this material.

As shown on FIG. 5, a RF gate 49 receiving the signal at the frequency $f_u$ from the generator 48 and the signal at the frequency f from the generator 36 produces a signal at the frequency $f_u$ modulated in intensity (or pulsed) at the frequency f, which is supplied to the transducer 15 of FIG. 4 after having been amplified through a RF power amplifier 50.

It is also possible to calibrate the above-defined ultrasonic absorption meter apparatus as outlined below. This calibration can also be considered as a variant of the measuring method of the present invention.

The calibration requires to vary a physical parameter of the specimen or sample 1 which changes the absorption of the material constituting this sample. This can be done for example by applying a magnetic field in the case of steels, applying a stress, varying the temperature, irradiating the specimen, etc. The infrared detector 21 records the change of infrared radiation emission from the sample 1, which change is proportional to the change of absorption. One may write, keeping the ultrasonic power at the same value:

$$\frac{\Delta\tau}{\tau} = \frac{\Delta\alpha}{\alpha} \quad (5)$$

where $\alpha$ is the absorption coefficient, $\Delta\alpha$ is its change, $\tau$ is the surface temperature modulation which is measured before the change of the parameter and $\Delta\tau$ is its variation measured through the above described apparatus according to the invention and caused by the physical parameter variation (in the cases where the temperature is not varied and the same location is viewed on the sample, $\Delta\tau/\tau$ is simply equal to the relative variation of infrared radiation). At the same time, the laser interferometric probe monitors the change of displacement $\Delta U$ caused by the change of attenuation of the ultrasonic wave beam inside the material of the sample 1 due to the physical parameter variation. This change of attenuation is equal to the change of the absorption coefficient $\Delta\alpha$ if the size and distribution of the inhomogeneities (grains in metals) has not changed; this is true if a field is applied, but this limits in general the range of temperature variation allowed. If there is no change at the emission of the ultrasonic wave beam, which is generally the case if the transducer 15 is kept in place, one may write:

$$\frac{\Delta U}{U} = e^{-\Delta\alpha d} \qquad (6)$$

where the displacexent U is measured by the probe before varying the physical parameter of the specimen and d is the distance between the emitting transducer 15 and the probed surface area of the sample 1. Equation 6 gives $\Delta\alpha$ which when introduced into equation 5, gives $\alpha$ (in absolute value). These calculations can of course be performed through the micro-computer 40. Thus, the instrument is calibrated and the proportionality constant between $\tau/U^2$ and $\alpha$ is determined. Alternatively, instead of using the laser interferometric probe, a conventional ultrasonic technique which uses a piezoelectric transducer may be used to measure the change in attenuation. In some cases, a conventional pulse echo technique may also be used: by monitoring the change of height of one echo, we determine the change in attenuation.

Possible uses of the method and of the ultrasonic absorption meter apparatus according to the present invention are outlined below:

Identification and sorting of metal alloys.

Characterisation of the effect of cold work on metals. One could check the uniformity of work on a rolled plate and verify in an industrial mill the uniformity of the production. Such a meter apparatus can be a useful research tool for the current developments in controlled rolling.

Detection and measurement of residual stress in metals, which residual stress affects the dislocations parameters and the orientation of magnetic domains and therefore change the ultrasonic absorption. By scanning the surface of the specimen (for example a piece with a weldment) stressed region can be found and the stress level can be determined after some calibration. Information on the direction of the stress can be obtained by changing the direction of the launched ultrasonic wave or its polarisation. Such a measurement is independent of the grain size and of the texture of the material, unlike other ultrasonic measurements techniques.

Detection and measurement of fatigue in materials (metals, ceramics, composites). Since fatigue is essentially a surface phenomenon, a surface wave is preferably used in this case. The meter apparatus is scanned over the region of the sample subjected to the ultrasonic wave beam. Fatigued areas will produce a change of absorption and will be detected in this way. Unlike other "fatigue meter apparatuses" which can only be used for fatigue tests, this meter will enable to check the state of fatigue of pieces which are in service.

The present invention has been described in details hereinabove with reference to preferred embodiments thereof, but it should be noted that such preferred embodiments can be modified at will within the scope of the appended claims without changing or altering the inventive idea and nature of the present invention.

The embodiments of the invention in which an exclusive property or privilege is claimed are defined as follows:

1. A method for determining at least one property of a material by measuring ultrasonic absorption in said material, said ultrasonic absorption being representative of said at least one property, said method comprising the steps of:
   subjecting a probed region of said material to an ultrasonic wave having an intensity varying in time;
   measuring a temperature modulation at a surface area of said material, said surface area corresponding to said probed region, and said surface temperature modulation being produced by absorption in said probed region of said ultrasonic wave;
   measuring an ultrasonic power over the probed region; and
   calculating said ultrasonic absorption in the probed region from said measured surface temperature modulation and said measured ultrasonic power for the purpose of determining said at least one property.

2. The method of claim 1, wherein said ultrasonic power measuring step comprises the step of measuring a surface displacement of said material surface area, said surface displacement being representative of said ultrasonic power over the probed region.

3. The method of claim 2, wherein said calculating step includes the step of dividing said measured temperature modulation by the square of said measured surface displacement to obtain a value representative of the ultrasonic absorption in the probed region.

4. The method of claim 2, wherein said calculating step comprises a calculation of an exact value of the ultrasonic absorption from said measured temperature modulation, and from said measured surface displacement, taking into consideration the profile of a beam formed by said ultrasonic wave, a distribution of ultrasonic energy in the probed region, and thermal properties of said material.

5. The method of claim 1, wherein said temperature modulation measuring step comprises a non-contact measurement of the temperature at said material surface area.

6. The method of claim 5, wherein said noncontact temperature measurement includes a detection of an infrared radiation, which infrared radiation is emitted by said surface area of the material.

7. The method of claim 1 wherein said temperature modulation is measured independently of a local emissivity of said surface area.

8. The method of claim 1, wherein the intensity of said ultrasonic wave is modulated at a predetermined frequency.

9. A method for determining at least one property of a material by measuring ultrasonic absorption in said material, said ultrasonic absorption being representative of said at least one property, said method comprising the steps of:
   subjecting said material to an ultrasonic wave having an intensity varying in time;
   subjecting said material to an external cause for varying the ultrasonic absorption of the material;
   measuring a relative variation of a temperature modulation at a surface area of said material, said surface area corresponding to a region of said material subjected to said ultrasonic wave, said temperature modulation being generated by absorption of the ultrasonic wave in the material, and said relative variation of the temperature modulation being due to said external cause and being representative of a relative variation of ultrasonic absorption in said material;

measuring a variation of attenuation of said ultrasonic wave in the material, due to said external cause; and calculating said ultrasonic absorption in the material from said measured temperature modulation relative variation and from said measured attenuation variation for the purpose of determining said at least one property.

10. The method of claim 9, in which said step of measuring the temperature modulation relative variation includes the step of measuring the temperature modulation at said surface area before said material is subjected to the external cause, and the step of measuring an absolute variation of said temperature modulation due to said external cause.

11. The method of claim 9, wherein said attenuation variation measuring step comprises the step of measuring a variation, caused by said external cause, of a surface displacement of said surface area, said surface displacement variation being representative of said variation of the ultrasonic wave attenuation.

12. The method of claim 11, wherein said calculating step comprises the step of calculating a variation of an absorption coefficient of said material from said measured surface displacement variation and from a measure of the surface displacement of said surface area before said material is subjected to said external cause, and the step of calculating the absolute value of the absorption coefficient of the material from said calculated absorption coefficient variation and from said measured temperature modulation relative variation.

13. The method of claim 9, wherein said external cause is the application of a magnetic field to said material.

14. The method of claim 9, wherein the intensity of said ultrasonic wave is modulated at a predetermined frequency.

15. The method of claim 9, wherein said temperature modulation relative variation measuring step includes a non-contact measurement of the temperature at said surface area of the material.

16. The method of claim 15, wherein said noncontact temperature measurement includes a detection of an infrared radiation, which infrared radiation is emitted by said surface area of the material.

17. The method of claim 9, wherein said external cause is the application of a stress to said material.

18. The method of claim 9, wherein said external cause is a variation of the temperature of the material.

19. The method of claim 9, wherein said external cause is irradiation of the material.

20. A device for determining at least one property of a material by measuring ultrasonic absorption in said material, said ultrasonic absorption being representative of said at least one property, said device comprising:

means for generating an ultrasonic wave having an intensity varying in time, and for subjecting a probed region of said material to said ultrasonic wave;

means for measuring a temperature modulation at a surface area of said material, said surface area corresponding to said probed region, and said surface temperature modulation being produced by absorption in the probed region of said ultrasonic wave;

means for measuring an ultrasonic power over the probed region; and means for calculating the ultrasonic absorption in the probed region from said measured surface temperature modulation and said measured ultrasonic power for the purpose of determining said at least one property.

21. The device of claim 20, wherein said subjecting and generating means comprise an ultrasonic transducer mounted on a metallic wedge disposed on said material through a coupling fluid, said ultrasonic transducer comprising means to generate said ultrasonic wave which is transmitted to said material through the metallic wedge and the coupling fluid.

22. The device of claim 21, in which said subjecting and generating means comprise means for supplying to said ultrasonic transducer a signal having a first frequency and being modulated in amplitude at a second frequency.

23. The device of claim 20, wherein said generating means comprise means for modulating said ultrasonic wave at a predetermined frequency.

24. The device of claim 20, in which said temperature modulation measuring means include means for measuring in a non-contact manner the temperature at said material surface area.

25. The device of claim 24, in which said noncontact temperature measuring means comprise means for detecting an infrared radiation emitted from said material surface area.

26. The device of claim 25, wherein said infrared energy detecting means include an infrared detector, first and second optic means disposed between said infrared detector and said surface area of the material for directing the infrared radiation towards said infrared detector which delivers an output signal representative of said infrared radiation, and a chopping blade mounted between said first and second optic means, which chopping blade oscillating at first frequency for repeatedly intercepting said infrared radiation at said first frequency, so that a chopped infrared radiation is supplied to said infrared detector.

27. The device of claim 26, in which said generating means comprise means for modulating the intensity of said ultrasonic wave at a second frequency, said temperature modulation measuring means comprising a first lock-in amplifier tuned to said first frequency, receiving said output signal from the infrared detector and producing a magnitude and a phase output signals, and a second lock-in amplifier tuned to said second frequency, receiving said magnitude output signal from the first lock-in amplifier and producing a magnitude output signal, said two lock-in amplifiers allowing a measurement of the temperature modulation independently of a local emissivity of said surface area.

28. The device of claim 27, wherein said temperature modulation measuring means comprise means for measuring the temperature of said chopping blade, means for measuring an average temperature of said material, and a microcomputer which comprises means to calculate said surface temperature modulation in response to said measured chopping blade temperature, said measured average temperature of the material, said phase output signal from the first lock-in amplifier, said magnitude output signal from the second lock-in amplifier, and an average value of said magnitude output signal from the first lock-in amplifier.

29. The device of claim 20, wherein said ultrasonic power measuring means comprises means for measuring a displacement of said material surface area, said surface displacement being representative of said ultrasonic power over the probed region.

30. The device of claim 29, in which said displacement measuring means comprise an interferometric probe, which interferometric probe including:
   a laser associated with an acousto-optic cell for generating a first and a second laser beam at a first and a second frequency, respectively, the second frequency being shifted with respect to the first frequency by a predetermined shifting frequency; and
   an optical detector receiving the first laser beam after reflection thereof on said surface area of the material, as well as the second laser beam, and delivering an output signal representative of a combination of said two laser beams received by said optical detector.

31. The device of claim 30, wherein said generating means comprises means for generating said ultrasonic wave at a third frequency and for modulating the intensity of said ultrasonic wave at a fourth frequency, and wherein said displacement measuring means further comprises in series:
   an amplifier with voltage-controlled gain for amplifying said output signal from the optical detector and for delivering a constant-level signal representative of this output signal from the optical detector;
   a high frequency lock-in amplifier tuned to a frequency determined by the following substraction: the predetermined shifting frequency minus said third frequency, which high frequency lock-in amplifier receiving said constant-level signal and delivering a magnitude output signal; and
   an averager or a lock-in amplifier tuned to said fourth frequency for receiving said magnitude output signal and for delivering an output signal representative of said displacement of said surface area of the material.

32. The device of claim 29, wherein said means for calculating the ultrasonic absorption in the probed region comprises means for dividing said measured temperature modulation by the square of said measured surface displacement in order to provide an output representative of said ultrasonic absorption in the probed region.

33. A device for determining at least one property of a material by measuring ultrasonic absorption in said material, said ultrasonic absorption being representative of said at least one property, said device comprising:
   means for generating an ultrasonic wave having an intensity varying in time, and for subjecting the material to said ultrasonic wave;
   means for subjecting said material to an external cause, said external cause changing the ultrasonic absorption of the material;
   means for measuring a relative variation of a temperature modulation at a surface area of said material, said surface area corresponding to a region of said material subjected to the ultrasonic wave, said temperature modulation being generated by absorption of the ultrasonic wave in the material, and said relative variation of the temperature modulation being due to said external cause and being representative of a relative variation of ultrasonic absorption in said material;
   means for measuring a variation of attenuation of the ultrasonic wave in said material due to said external cause; and
   means for calculating said ultrasonic absorption in the material from said measured relative variation of the temperature modulation and from said measured attenuation variation for the purpose of determining said at least one property.

34. The device of claim 33, wherein which said means for measuring the relative variation of the temperature modulation includes means for measuring the temperature modulation at said surface area of the material before said material is subjected to the external cause, and means for measuring an absolute variation of said temperature modulation due to said external cause.

35. The device of claim 33, wherein said means for measuring the attenuation variation comprise means for measuring a variation, caused by said external cause, of a surface displacement of said surface area, said surface displacement variation being representative of said variation of the ultrasonic wave attenuation.

36. The device of claim 35, wherein said calculating means comprises means for calculating a variation of an absorption coefficient of said material from said measured surface displacement variation and from a measure of the surface displacement of said surface area before said material is subjected to said external cause, and means for calculating the absolute value of the absorption coefficient of the material from said calculated absorption coefficient variation and from said measured temperature modulation relative variation.

37. The device of claim 33, wherein said means for subjecting the material to an external cause comprises means for applying a magnetic field to said material.

38. The device of claim 33, wherein said generating means comprise means for modulating the intensity of said ultrasonic wave at a predetermined frequency.

39. The device of claim 33, wherein said means for measuring the temperature modulation relative variation include means for measuring the temperature at said surface area of the material in a non-contact manner.

40. The device of claim 39, wherein said noncontact temperature measuring means include means for detecting an infrared radiation emitted by said surface area of the material.

41. The device of claim 33, wherein said means for measuring the attenuation variation comprises a piezoelectric transducer.

42. The device of claim 34, comprising means for measuring said temperature modulation independently of a local emissivity of said surface area.

43. The device of claim 33, wherein said means for subjecting the material to an external cause comprises means for applying a stress to said material.

44. The device of claim 33, wherein said means for subjecting the material to an external cause comprises means for varying the temperature of the material.

45. The device of claim 33, wherein said means for subjecting the material to an external cause comprises means for irradiating said material.

* * * * *